(12) United States Patent
Keusenkothen et al.

(10) Patent No.: US 10,099,972 B2
(45) Date of Patent: Oct. 16, 2018

(54) METHODS AND SYSTEMS FOR PRODUCING LIQUID HYDROCARBONS

(71) Applicants: Paul F. Keusenkothen, Houston, TX (US); Timothy A. Barckholtz, Whitehouse Station, NJ (US); J. Tim Cullinane, Easton, PA (US); Robert D. Denton, Bellaire, TX (US); Frank Hershkowitz, Basking Ridge, NJ (US); Ian J. Laurenzi, Hampton, NJ (US)

(72) Inventors: Paul F. Keusenkothen, Houston, TX (US); Timothy A. Barckholtz, Whitehouse Station, NJ (US); J. Tim Cullinane, Easton, PA (US); Robert D. Denton, Bellaire, TX (US); Frank Hershkowitz, Basking Ridge, NJ (US); Ian J. Laurenzi, Hampton, NJ (US)

(73) Assignee: ExxonMobil Upstream Research Company, Spring, TX (US)

( * ) Notice: Subject to any disclaimer, the term of this patent is extended or adjusted under 35 U.S.C. 154(b) by 891 days.

(21) Appl. No.: 14/531,725

(22) Filed: Nov. 3, 2014

(65) Prior Publication Data
US 2015/0158789 A1    Jun. 11, 2015

Related U.S. Application Data

(60) Provisional application No. 61/913,009, filed on Dec. 6, 2013.

(51) Int. Cl.
*C07C 2/80* (2006.01)
*C07C 2/76* (2006.01)

(52) U.S. Cl.
CPC .......... *C07C 2/80* (2013.01); *C07C 2/76* (2013.01); *C07C 2529/40* (2013.01)

(58) Field of Classification Search
CPC ...... C07C 2/76–2/84; C07C 2529/40–2529/48; F02C 6/18
See application file for complete search history.

(56) References Cited

U.S. PATENT DOCUMENTS 3,449,243 A * 6/1969 Strong, Jr. .......... C10G 17/04
                                              208/251 R
3,463,612 A * 8/1969 Whitsel, Jr. ............ B01J 3/08
                                              422/152

(Continued)

FOREIGN PATENT DOCUMENTS

EP    1106788    6/2001   ............ F01K 23/06
GB    2191212    12/1987  ............... C07C 2/00

(Continued)

OTHER PUBLICATIONS

Bal'zhinimaev, B. S. et al. (2011) "Innovative Russian Approaches to Catalysts for Oil Refinery and Petrochemistry," *Abstract-241st ACS Nat'l Mtg & Expo.*, Anaheim, CA, Mar. 27-31.

(Continued)

*Primary Examiner* — Jason Shanske
*Assistant Examiner* — Jessica Kebea
(74) *Attorney, Agent, or Firm* — ExxonMobil Upstream Research Company—Law Department (57) ABSTRACT

Systems and a method are provided for producing an aromatic hydrocarbon and generating electricity from a tail gas stream. The method includes feeding a first stream including a raw natural gas into a reactor. The method includes converting the first stream, at least in part, to a second stream including an aromatic hydrocarbon within the reactor. The method includes separating the second stream into a tail gas stream and a liquid aromatic hydrocarbon stream and combusting at least a portion of the tail gas stream to generate electricity.

11 Claims, 6 Drawing Sheets

(56) References Cited

U.S. PATENT DOCUMENTS

| | | | |
|---|---|---|---|
| 3,702,886 A | 11/1972 | Argauer et al. | 423/328 |
| 3,709,979 A | 1/1973 | Chu | 423/328 |
| 3,832,449 A | 8/1974 | Rosinski et al. | 423/328 |
| 3,857,685 A * | 12/1974 | Lehman | C10G 47/00 208/103 |
| 4,016,218 A | 4/1977 | Haag et al. | 260/671 |
| 4,016,245 A | 4/1977 | Plank et al. | 423/328 |
| 4,076,842 A | 2/1978 | Plank et al. | 423/328 |
| RE29,948 E | 3/1979 | Dwyer et al. | 208/110 |
| 4,229,424 A | 10/1980 | Kokotailo | 423/328 |
| 4,234,231 A | 11/1980 | Yan | 299/4 |
| 4,520,217 A * | 5/1985 | Minet | C07C 2/00 208/130 |
| 4,556,477 A | 12/1985 | Dwyer | 208/111 |
| 4,597,257 A * | 7/1986 | Schuster | F02B 43/08 60/39.12 |
| 4,677,235 A * | 6/1987 | Mowry | C07C 2/76 585/415 |
| 4,795,844 A * | 1/1989 | Martindale | C07C 2/00 585/415 |
| 4,881,366 A * | 11/1989 | Nurse | C01B 3/48 60/39.12 |
| 5,138,113 A * | 8/1992 | Juguin | C07C 2/76 585/322 |
| 5,614,159 A * | 3/1997 | Modic | B01D 53/72 423/245.3 |
| 6,130,260 A | 10/2000 | Hall et al. | 518/703 |
| 8,455,707 B2 | 6/2013 | Hershkowitz et al. | 585/535 |
| 9,803,505 B2 * | 10/2017 | Noureldin | C10G 59/00 |
| 2002/0177629 A1 * | 11/2002 | O'Beck | C01B 3/382 518/703 |
| 2003/0144565 A1 * | 7/2003 | Allison | C07C 2/76 585/418 |
| 2007/0129587 A1 | 6/2007 | Iaccino et al. | 585/407 |
| 2007/0260098 A1 * | 11/2007 | Iaccino | C07C 2/76 585/412 |
| 2008/0293980 A1 * | 11/2008 | Kiesslich | B01J 29/46 585/408 |
| 2009/0247804 A1 | 10/2009 | Sauer et al. | 585/733 |
| 2010/0185034 A1 | 7/2010 | Nishimura et al. | 585/420 |
| 2010/0256245 A1 | 10/2010 | Iaccino et al. | 518/702 |
| 2011/0288355 A1 * | 11/2011 | Ogawa | B01J 29/48 585/400 |
| 2012/0036889 A1 | 2/2012 | Denton et al. | 62/618 |
| 2015/0259610 A1 * | 9/2015 | Yanagawa | C10G 11/05 585/400 |

FOREIGN PATENT DOCUMENTS

| | | | |
|---|---|---|---|
| GB | 2191212 A * | 12/1987 | C07C 2/76 |
| RU | 2185239 | 7/2002 | B01J 23/83 |
| RU | 2186755 | 8/2002 | C07C 2/00 |
| RU | 2188225 | 8/2002 | B01J 29/04 |
| RU | 2227793 | 4/2004 | C07C 2/76 |
| RU | 2271863 | 3/2006 | B01J 29/48 |
| RU | 2296009 | 3/2007 | B01J 29/46 |
| RU | 2302291 | 7/2007 | B01J 21/04 |
| RU | 2305594 | 9/2007 | B01J 8/02 |
| RU | 2006/111295 | 10/2007 | B01J 23/30 |
| RU | 2333033 | 9/2008 | B01J 23/06 |
| RU | 2408425 | 12/2009 | B01J 23/50 |
| WO | WO1999/006502 | 4/1999 | C01B 3/26 |
| WO | WO 2007053061 A2 * | 5/2007 | C10G 29/205 |
| WO | WO2007/091912 | 8/2007 | C10G 59/02 |

OTHER PUBLICATIONS

Echevsky G.V. et al. (2001) "A New One-Step $CH_4$ and $C_3$—$C_4$ Paraffins Co-Processing Into Aromatic Hydrocarbons," *Int'l Gas Research Conf. Proc.*, 10 pgs, 7 tables, map.

Echevsky G.V. et al. (2004) "Direct Insertion of Methane Into $C_3$—$C_4$ Paraffins Over Zeolite Catalysts: A Start to the Development of New One-Step Catalytic Processes for the Gas-to-Liquid Transformation," *Applied Catalysis A: General*, v.258(2004), pp. 159-171.

Echevsky G.V. et al. (2005) "Relation Between Hydro-Dehydrogenating and Acid Functions of Zeolite Catalysts and Their Effectiveness in Aromatization of Light Paraffins," *Reaction Kinetics and Catalysis Letters*, v. 84(2), pp. 367-373.

Gabrienko, A. A. et al. (2010) "Metal-Alkyl Species are Formed on Interaction of Small Alkanes With Gallium Oxide: Evidence from Solid-State NMR," *Chemical Physics Letters*, v.496(1-3), pp. 148-151.

Gabrienko, A. A. et al. (2011) "Hydrogen H/D Exchange and Activation of $C_1$-n-$C_4$ Alkanes on Ga-Modified Zeolite BEA Studied with $^1$H Magic Angle Spinning Nuclear Magnetic Resonance in Situ," *Jrnl. of Physical Chemistry*, v.115(28), pp. 13877-13886.

Gabrienko, A. A. et al. (2013) "Methane Activation and Transformation on Ag/H-ZSM-5 Zeolite Studied With Solid-State NMR," *Jrnl. Phys. Chemistry*, v.117(15), pp. 7690-7702.

Guo, Jianjun et al. (2009) "Review: Energy-Efficient Coaromatization of Methane and Propane," *Jrnl of Natural Gas Chemistry*, v.18, pp. 260-272.

Ismagilov, Z. R. et al. (2005) "Carbonization and Regeneration of Mo/ZSM-5 Catalysts for Methane Dehydroaromatization," *Eurasian Chemico-Technological Jrnl.*, v.7(2), pp. 115-121.

Ismagilov, Z. R. et al. (2008) "Direct Conversion of Methane on Mo/ZSM-5 Catalysts to Produce Benzene and Hydrogen: Achievements and Perspectives," *Energy & Env. Sci.*, v.1(5), pp. 526-541.

Ismagilov, Z. R. et al. (2010) "Structural Changes of Mo/ZSM-5 Caralysts During the Methane Dehydroaromatization," *Eurasian Chemico-Technological Jrnl.*, v.12(1), pp. 9-16.

Ismagilov, Z. R. et al. (2011) "Methane Conversion to Valuable Chemicals Over Nanostructured Mo/ZSM-5 Catalysts," *Petroleum Chemistry*, v. 51(3), pp. 174-186.

Luzgin, M. V. et al. (2008) "Understanding Methane Aromatization on a Zn-Modified High-Silica Zeolite," *Angewandte Chemei, Int'l Ed.*, v.47(24), pp. 4559-4562.

Luzgin, M. V. et al. (2009) "Methane Aromatization on Zn-Modified Zeolite in the Presence of a Co-Reactant Higher Alkane: How does it occur?," *Catalysis Today*, v.144(3-4), pp. 265-272.

Luzgin, M. V. et al. (2010) "The "Alkyl" and "Carbenium" Pathways of Methane Activation on Ga-Modified Zeolite BEA: 13C Solid-State NMR and GC-MS Study of Methane Aromatization in the Presence of Higher Alkane," *Jrnl. of Phys. Chem.*, v.114(49), pp. 21555-21561.

Matus, E. V. et al. (2003) "Mo/ZSM-5 Catalysts for Methane Aromatization. Study of the Mo Precursor Species in Impregnation Solution of Ammonium Heptamolybdate," *Khimiya v Interesakh Ustoichivogo Razvitiya*, v. 11(1), pp. 167-171.

Matus, E. V. et al. (2007) "Study of Methane Dehydroaromatization and Impregnated Mo/ZSM-5 Catalysts and Characterization of Nanostructured Molybdenum Phases and Carbonaceous Deposits," *Industrial & Engineering Chemistry Research*, v.46(12), pp. 4063-4074.

Matus, E. V. et al. (2009) "Peculiarities of Dehydroaromatization of CH4—C2H6 and CH4 over Mo/ZSM-5 Catalysts," *Reaction Kinetics and Catalysis Letters*, v. 98(1), pp. 59-67.

Matus, E. V. et al. (2010) "Deactivation and Regeneration of Mo/ZSM-5 Catalysts for Methane Dehydroaromatization," *Eurasian Chemico-Technological Jrnl.*, v.12(1), pp. 1-8.

Stepanov, A. G. (2010) "Results of NMR Spectroscopic Studies of Hydrocarbon Conversions on Solid Acid Catalysts in the Last 25 Years," *Kinetics and Catalysis*, v. 51(6), pp. 854-872.

Vasenin, N. T. et al. (2005) "Effect of Thermal Treatment on States of Molybdenum in Mo/H-ZSM-5 Catalyst for Methane Dehydroaromatization: ESR and UV-VIS Study," *Topics in Catalysis*, v. 32(1-2), pp. 61-70.

Zaikovskii, V. I. et al. (2005) "The State of the Active Sites and Deactivation of Mo-ZSM-5 Catalysts of Methane Dehydroaromatization," *Doklady Physical Chemistry*, v. 404(2), pp. 201-204.

Zaikovskii, V. I. et al. (2006) "Properties and Deactivation of the Active Sites of an MoZSM-5 Catalyst for Methane Dehydroaromatization: Electron Microscopic and EPR Studies," *Kinetics and Catalysis*, v. 47(3), pp. 389-394.

(56) References Cited

OTHER PUBLICATIONS

Zhidomirov, G. M. et al. (2004) "Structure and Reactivity of Metal Ion Species in High-Silica Zeolites," *Computer Modelling of Microporous Materials*, pp. 201-241.

\* cited by examiner

METHODS AND SYSTEMS FOR PRODUCING LIQUID HYDROCARBONS

CROSS REFERENCE TO RELATED APPLICATIONS

This application claims the priority benefit of U.S. Patent Application 61/913,009 filed Dec. 6, 2013 entitled METHODS AND SYSTEMS FOR PRODUCING LIQUID HYDROCARBONS, the entirety of which is incorporated by reference herein.

In addition U.S. Provisional patent application No. 61/913,009 is related to but does not claim priority to ExxonMobil Chemical Company's U.S. Provisional patent application No. 61/912,877 filed on Dec. 6, 2013 entitled HYDROCARBON CONVERSION; U.S. Provisional patent application No. 61/912,866 filed on Dec. 6, 2013 entitled PRODUCTION OF C2+ OLEFINS; U.S. Provisional patent application No. 61/912,886 filed on Dec. 6, 2013 entitled PRODUCTION OF C2+ OLEFINS; and U.S. Provisional patent application No. 61/912,901 filed on Dec. 6, 2013 entitled HYDROCARBON CONVERSION.

FIELD

The present techniques generally relate to producing an aromatic hydrocarbon stream and generating power. Particularly, the present techniques provide for the conversion of raw natural gas into an aromatic hydrocarbon stream and the generation of electricity from a tail gas stream.

BACKGROUND

This section is intended to introduce various aspects of the art, which may be associated with exemplary embodiments of the present techniques. This description is believed to assist in providing a framework to facilitate a better understanding of particular aspects of the present techniques. Accordingly, it should be understood that this section should be read in this light, and not necessarily as admissions of prior art.

Some processing technologies provide for the conversion of a high quality gas into longer-chain hydrocarbons. As used herein a "high quality gas" can be formed by purification and fractionation to form a narrow molecular weight material. For example, recovered raw natural gas may be separated from recovered crude oil and later processed for the removal of water, natural gas condensate, acid gases, and other contaminants, and then fractionated into different molecular weight components to produce the high quality gas. The purification and fractionation may be done before the gas product is converted into the higher molecular weight hydrocarbons. This may be due in part to mainline transportation systems imposing restrictions on the make-up of the hydrocarbons before entry into additional processing units, pipelines facilities, or storage.

The technologies for the process of converting the high quality gas into the higher molecular weight hydrocarbons include relatively well-known and well-proven techniques that have been in development through the years. One example of a process that can convert a gas product into higher molecular weight hydrocarbons may include the Cyclar™ process from UOP. The Cyclar™ process is a non-integrated chemical production facility that converts liquefied petroleum gas (LPG) directly into a liquid, aromatic product. Particularly, the Cyclar™ process provides a process for upgrading lower value propane and butane ($C_3/C_4$ hydrocarbons) into a higher value, liquid aromatic concentrate (benzene, toluene, xylene, or "BTX") that may be used as feedstock to an aromatics complex. The process may be typically operated at temperatures higher than 800° F. (425° C.). Another process is the Choudhary process, which also converts a percentage of methane, along with the $C_3/C_4$ hydrocarbons, to yield up to a 30% conversion of the methane along with a higher conversion rate of the $C_3/C_4$ hydrocarbons. See Journal of Natural Gas Chemistry 18 (2009) 260-272, Review: Energy-Efficient coaromatization of methane and propane, Jianjun Guo, Hui Lou, Xiaoming Zheng.

The Fischer-Tropsch process can also be used to convert hydrocarbons or natural gas into higher molecular weight hydrocarbons. The Fischer-Tropsch process is an exothermic conversion process including a collection of chemical reactions that can convert a mixture of carbon monoxide and hydrogen into liquid hydrocarbons. The more useful reactions produce mostly straight-chain alkanes, suitable for diesel fuel. Generally, the Fischer-Tropsch process is operated in the temperature range of 302° F. to 572° F. In this case, higher temperatures lead to faster reactions and higher conversion rates while favoring methane production. An increase in pressure in the process leads to higher conversion rates and also favors the formation of long-chained alkanes, both of which are desirable. Typical pressures can range from one to several tens of atmospheres.

Another process is the RZ™ Platforming process from UOP. The RZ™ Platforming process is designed to efficiently convert paraffins and naphthenes to aromatics with limited ring opening or cracking. Specifically, the RZ™ Platforming process utilizes a fixed bed system for the production of high yields of benzene toluene (BT) aromatics and hydrogen. Additionally, the Aromax® Process from Chevron Phillips selectively converts light paraffins and naphthenes to both hydrogen and aromatic products utilizing fixed-bed reforming equipment. The aforementioned process are just a few of the techniques used to convert high quality gas into aromatic products.

U.S. Patent Application Publication No. 2012/0036889 by Denton et al. discloses a methane conversion process. The process includes the conversion of a gaseous hydrocarbon feed, including methane, to an aromatic hydrocarbon. The methane conversion process is integrated with a liquefied natural gas (LNG) and/or pipeline gas process. In operation, the gaseous hydrocarbon stream is feed to a conversion zone with specified parameters to produce a gaseous effluent stream, including at least one aromatic compound, unreacted methane, and hydrogen.

U.S. Pat. No. 8,455,707 to Hershkowitz discloses a process for converting methane into acetylene and other higher hydrocarbons. The process includes a reverse-flow reactor system where first and second reactants are supplied in a first reactor bed such that both reactants serve to quench the reactor bed and to control combustion for thermal regeneration. See also U.S. Pat. No. 6,130,260 to Synfuels, which discloses converting methane into acetylene and then into liquid fuels.

U.S. Patent Application Publication No. 2007/0260098 by Iaccino et al. discloses the production of aromatic hydrocarbons from methane. The process includes a process to convert methane to aromatic hydrocarbons to produce first and second effluent streams. The hydrogen within the first effluent stream is reacted with an oxygen-containing species to produce a second effluent stream including a reduced hydrogen content.

U.S. Patent Application Publication No. 2009/0247804 by Sauer et al. discloses a method for converting methane to useful hydrocarbons. The process includes combining a methane/hydrogen fluid with a catalyst composition derived from an aluminum compound and a transition metal halide to produce higher molecular weight hydrocarbons.

Many other conversion process techniques exist for the production of aromatics from a high quality gas. However, the processes generally rely on an existing infrastructure, such as a chemical plant and purification systems. Accordingly, there is a need for an independent infrastructure process for the conversion of an unprocessed raw hydrocarbon gas to an aromatic product that may also incorporates other processing techniques including power generation and heat removal.

SUMMARY

An exemplary embodiment provides a method for producing liquid hydrocarbons and power. The method includes producing a first stream including methane. The method includes reacting the first stream in a reactor to form a second stream having at least a portion of the methane converted to a higher molecular weight hydrocarbon. The method includes separating the second stream into a tail stream that is enriched in methane and a product stream enriched in the higher molecular weight hydrocarbon. The method includes combusting at least a portion of the tail stream to generate power.

Another exemplary embodiment provides a system for producing liquid hydrocarbons from a first stream including methane and generating power. The system includes a reactor configured to convert the first stream into a second stream having at least a portion of the methane in the first stream converted to a higher molecular weight hydrocarbon. The system includes a separation vessel configured to separate the second stream into a tail gas stream and a liquid hydrocarbon stream. The system includes a combustor to combust the tail gas stream to generate power.

Another exemplary embodiment provides a method for producing an aromatic hydrocarbon and generating electricity from a tail gas stream. The method includes feeding a first stream including raw natural gas into an aromatic reactor. The method includes converting the first stream, at least in part, to a second stream including the aromatic hydrocarbon. The method includes separating the second stream into the tail gas stream and a liquid aromatic hydrocarbon stream. The method includes burning at least a portion of the tail gas stream in a gas turbine to generate the electricity.

DESCRIPTION OF THE DRAWINGS

The advantages of the present techniques are better understood by referring to the following detailed description and the attached drawings, in which.

DETAILED DESCRIPTION

In the following detailed description section, specific embodiments of the present techniques are described. However, to the extent that the following description is specific to a particular embodiment or a particular use of the present techniques, this is intended to be for exemplary purposes only and simply provides a description of the exemplary embodiments. Accordingly, the techniques are not limited to the specific embodiments described below, but rather, include all alternatives, modifications, and equivalents falling within the true spirit and scope of the appended claims.

At the outset, for ease of reference, certain terms used in this application and their meanings as used in this context are set forth. To the extent a term used herein is not defined below, it should be given the broadest definition persons in the pertinent art have given that term as reflected in at least one printed publication or issued patent. Further, the present techniques are not limited by the usage of the terms shown below, as all equivalents, synonyms, new developments, and terms or techniques that serve the same or a similar purpose are considered to be within the scope of the present claims.

The term "aromatic hydrocarbons" refers to molecules containing one or more aromatic rings. Examples of aromatic hydrocarbons are benzene, toluene, xylenes, naphthalene, and methylnaphthalenes The term "aromatic" refers to unsaturated compounds with at least one closed ring of at least 6 atoms, with all of the ring atoms being co-planar or almost co-planar and covalently linked, and with all of the ring atoms being part of a mesomeric system. As used herein, when the "aromatic" substituent is monocyclic, it preferably contains 6 ring atoms, and when the "aromatic" substituent is polycyclic, it preferably contains 10 ring atoms contained in fused rings.

The term "$C_n$" hydrocarbon refers to a hydrocarbon with "n" carbon atoms, and "$C_n$-$C_m$ hydrocarbons" represents hydrocarbons having between "n" and "m" carbon atoms.

The term "catalyst" refers to a material, which under certain conditions of temperature or pressure increases the rate of specific chemical reactions. A catalyst may also be a material that performs as a physisorbent or chemisorbent for specific components of the feed stream.

The term "chain length" may broadly refer to a number of atoms forming and/or making a backbone and/or structure of a molecule and/or compound, such as carbon atoms for a hydrocarbon.

The term "chemical reaction" refers to any process including the breaking or making of chemical bonds including a dissociation, recombination, or rearrangement of atoms.

The term "coke" refers to the solid residue remaining from the pyrolysis of hydrocarbons.

The term "crude oil" refers to hydrocarbons formed primarily of carbon and hydrogen atoms. The hydrocarbons may also include other elements, such as, but not limited to, halogens, metallic elements, nitrogen, oxygen, or sulfur. Hydrocarbons derived from an oil-bearing formation may include, but are not limited to, kerogen, bitumen, pyrobitumen, asphaltenes, resins, oils, or combinations thereof.

The term "fixed-bed reactor" refers to a reactor containing catalyst material typically in pellet form, packed in a static bed.

The term "gas turbine" refers to a unit including a compressor, a combustion chamber, and turbine mechanically connected to the compressor, most preferably connected on a common shaft. Generally, a gas turbine uses energy from burning a fuel in the combustion chamber to power a compressor that provides an oxidant stream to the combustion chamber. This is termed the Brayton cycle. A "turbine" is used in the meaning of an expansion unit for converting of the energy of high temperature gas to rotational energy.

The term "higher hydrocarbons" refers to hydrocarbon(s) having more than one carbon atom per molecule, oxygenate having at least one carbon atom per molecule, e.g., ethane, ethylene, propane, propylene, benzene, toluene, xylenes, naphthalene, and/or methyl naphthalene; and/or organic compound(s) including at least one carbon atom and at least one non-hydrogen atom, e.g., methanol, ethanol, methylamine, and/or ethylamine.

The term "hydrocarbon" refers to an organic compound that includes primarily, if not exclusively, the elements hydrogen and carbon. Hydrocarbons may also include other elements, such as, but not limited to, halogens, metallic elements, nitrogen, oxygen, and/or sulfur. Hydrocarbons generally fall into two classes: aliphatic, or straight chain hydrocarbons, and cyclic, or closed ring hydrocarbons, including cyclic terpenes. Examples of hydrocarbon-containing materials include any form of natural gas, oil, coal, and bitumen.

The term "hydrocarbon diluent" refers to any substance containing one or more hydrocarbon compounds and/or substituted hydrocarbon compounds, which is suitable for use for diluting a hydrocarbon in the practice of the invention. For example, a tail gas stream containing hydrocarbons may be an added diluent for natural gas.

The term "hydrocarbon stream" refers to a hydrocarbon or mixtures of hydrocarbons that are gases or liquids. For example, hydrocarbon fluids may include a hydrocarbon or mixtures of hydrocarbons that are gases or liquids at formation conditions, at processing conditions or at ambient conditions (15° C. and 1 atm pressure). Hydrocarbon fluids may include, for example, oil, natural gas, coalbed methane, shale oil, pyrolysis oil, pyrolysis gas, a pyrolysis product of coal, and other hydrocarbons that are in a gaseous or liquid state The term "light hydrocarbons" refer to hydrocarbons having carbon numbers in a range from 1 to 5.

The term "natural gas" refers to a multi-component gas obtained from a crude oil well (associated gas) or from a subterranean gas-bearing formation (non-associated gas). The composition and pressure of natural gas can vary significantly. A typical natural gas stream contains methane (C1) as a significant component. Raw natural gas may also contain ethane (C2), higher molecular weight hydrocarbons, acid gases (such as carbon dioxide, hydrogen sulfide, carbonyl sulfide, carbon disulfide, and mercaptans), and minor amounts of contaminants such as water, nitrogen, iron sulfide, wax, and crude oil. As used herein, natural gas includes gas resulting from the regasification of a liquefied natural gas, which has been purified to remove contaminates, such as water, acid gases, and most of the higher molecular weight hydrocarbons.

The term "high quality gas" refers to a gas that has undergone natural gas processing to separate various hydrocarbons and fluids from a raw natural gas. Also referred to as pipeline quality dry natural gas.

The term "raw natural gas" refers to a gas that is included of methane, but may also include numerous other light hydrocarbons including ethane, propane, and butanes. Higher molecular weight hydrocarbons, including pentanes, hexanes, and impurities like benzene may also be present in small amounts. Furthermore, raw natural gas may contain amounts of non-hydrocarbon impurities, such as nitrogen, hydrogen sulfide, carbon dioxide, and traces of helium, carbonyl sulfide, various mercaptans, and water.

The term "oil and gas reservoir" refers to a well or reservoir that is a subsurface zone that produces oil and/or gas and lacks communication other reservoirs. As used in the claims, "oil and gas well" and "oil and gas reservoir" are interchangeable.

The term "reservoir" refers to a formation or a portion of a formation that includes sufficient permeability and porosity to hold and transmit fluids, such as hydrocarbons or water.

Overview

Embodiments of the present disclosure provide a method and system for producing liquid hydrocarbons from unpurified, raw natural gas while generating power. More specifically, various embodiments may provide a raw hydrocarbon gas stream converted in a reactor, at least in part, to a higher molecular weight hydrocarbons stream. The reactor is endothermic and the heat supplied to the reaction may be generated in other units within the system. The separation of the higher molecular weight hydrocarbons stream may yield a liquid hydrocarbons stream and a tail gas stream where at least a portion of the tail gas may be combusted and utilized for power generation.

Raw natural gas recovered at a well-head usually contains impurities and contaminants including water vapor, hydrogen sulfide, carbon dioxide, nitrogen, and other compounds. However, most techniques for converting light hydrocarbons into aromatic, or heavy hydrocarbons, utilize a feedstock of purified hydrocarbons having 2 to 5 carbon atoms per molecule. Some of the methods for purification may include hydrogenation, dehydrogenation, sulfur, and acid gas removal techniques, among other processes, to remove the aforementioned impurities and contaminants. Thus, the purified hydrocarbon feed utilized in the conventional production of aromatic hydrocarbons usually includes propane, propylene, butanes, butylenes, with unsaturated compounds being preferred in many processes. Further, specific hydrocarbon reactants can be separated from the purified stream by fractionation. The resulting gaseous hydrocarbons may then be recycled or transported for further processing or commercialization.

However, in remote locations, the appropriate infrastructures may not exist to purify and fractionate the raw natural gas before it can be used. Thus, the recovery of raw natural gas may not outweigh the cost to implement the necessary facilities to remove, purify, and transport the natural gas from remote locations. Thus, the raw natural gas may be burned or flared as a byproduct of oil production. Unfortunately, flaring wastes the energy content of the gaseous hydrocarbons. Furthermore, flaring can pose a hazard to human health due to constituents that may be present in the natural gas, such as sulfur compounds.

Figure 1:
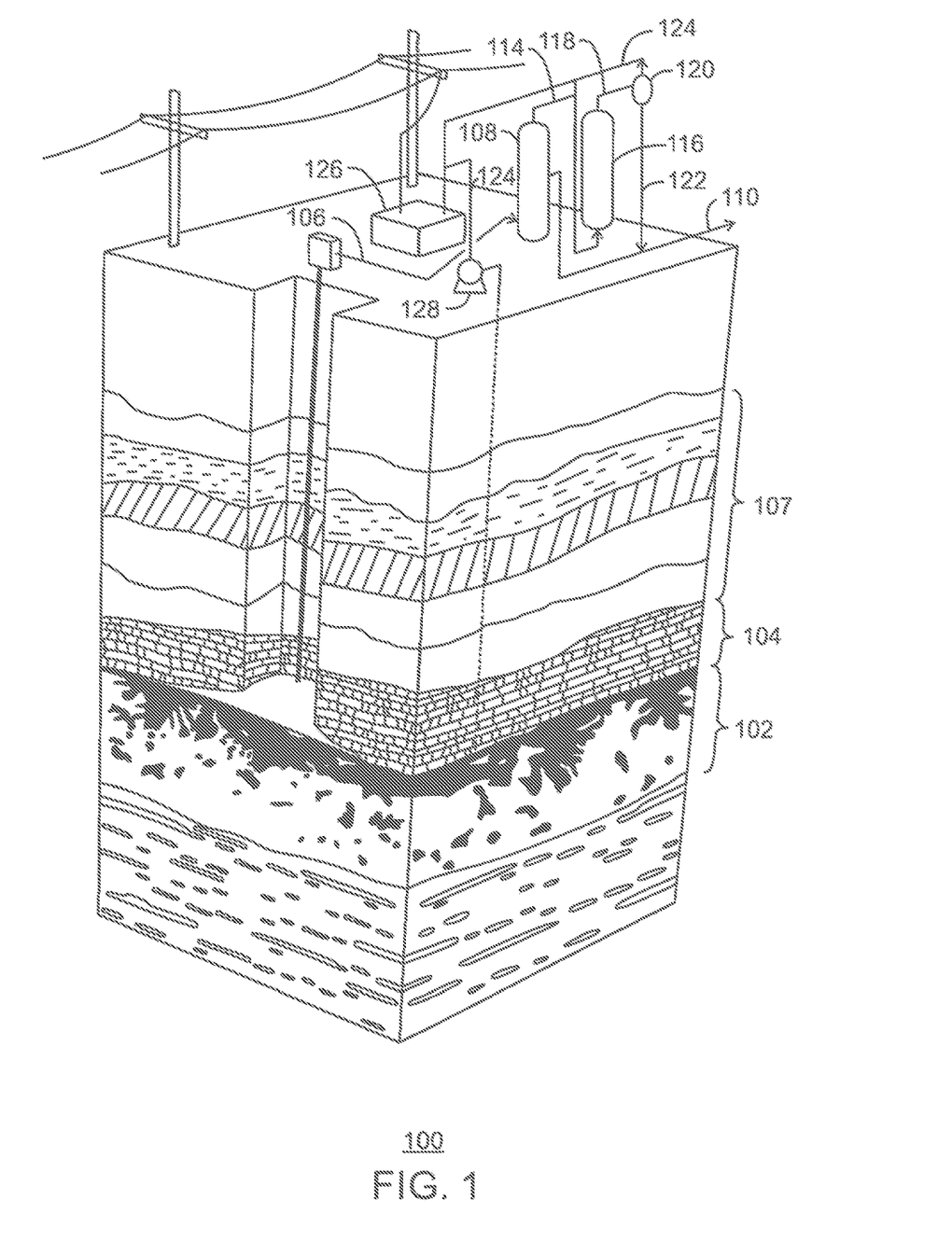
FIG. 1 is an illustration of an oil and gas well reservoir including trapped oil and gas within rock formations.

FIG. 1 is an illustration of an oil and gas well reservoir 100 including trapped oil and gas within rock formations. As shown in FIG. 1, an oil and gas well reservoir 100 can be a subsurface pool of hydrocarbons contained in porous sedimentary rock 102. A layer of impermeable rock formations, termed cap rock 104, may prevent the escape of the naturally occurring hydrocarbons into overlying sediment and rock formations 107 (the overburden). Various recovery methods may be implemented to extract and recover both the oil and gas hydrocarbons. During recovery, the oil and gas reservoir 100 may produce the crude oil and raw natural gas along with other liquid, gaseous, and solid hydrocarbons.

A hydrocarbon stream 106 can be produced from the reservoir 102, which may include gas, oil, water, and any combinations thereof. The hydrocarbon stream 106 can be flowed into a gas-oil separator 108, where the raw natural gas may be processed for the removal of an oil stream 110 including oil and other liquids. An overhead gas stream 114 from the gas-oil separator 108 may be further processed in a reactor 116.

The liquid/gas mixture stream 118 generated in the reactor 116 may flow to a separator 120 where a bottoms liquid stream 122 can be combined with the oil stream 110. A tail gas stream 124 may be produced overhead and later combusted, for example, in a gas turbine generator 126, to generate power. In some embodiments, the pressure in the reservoir 102 can be maintained by recycling a portion of the tail gas 124 back into the reservoir 100, via a compressor 128, to maintain the pressure of a gas cap located within the reservoir 100. The tail gas hydrogen content may be relatively high and processes known to those skilled in the art can be used to separate the tail gas into a hydrogen rich stream and hydrogen poor stream. Accordingly, the hydrogen poor tail gas can be reinjected via compressor 128, while the hydrogen rich stream can be used as fuel or recycled, as required.

Figure 2:
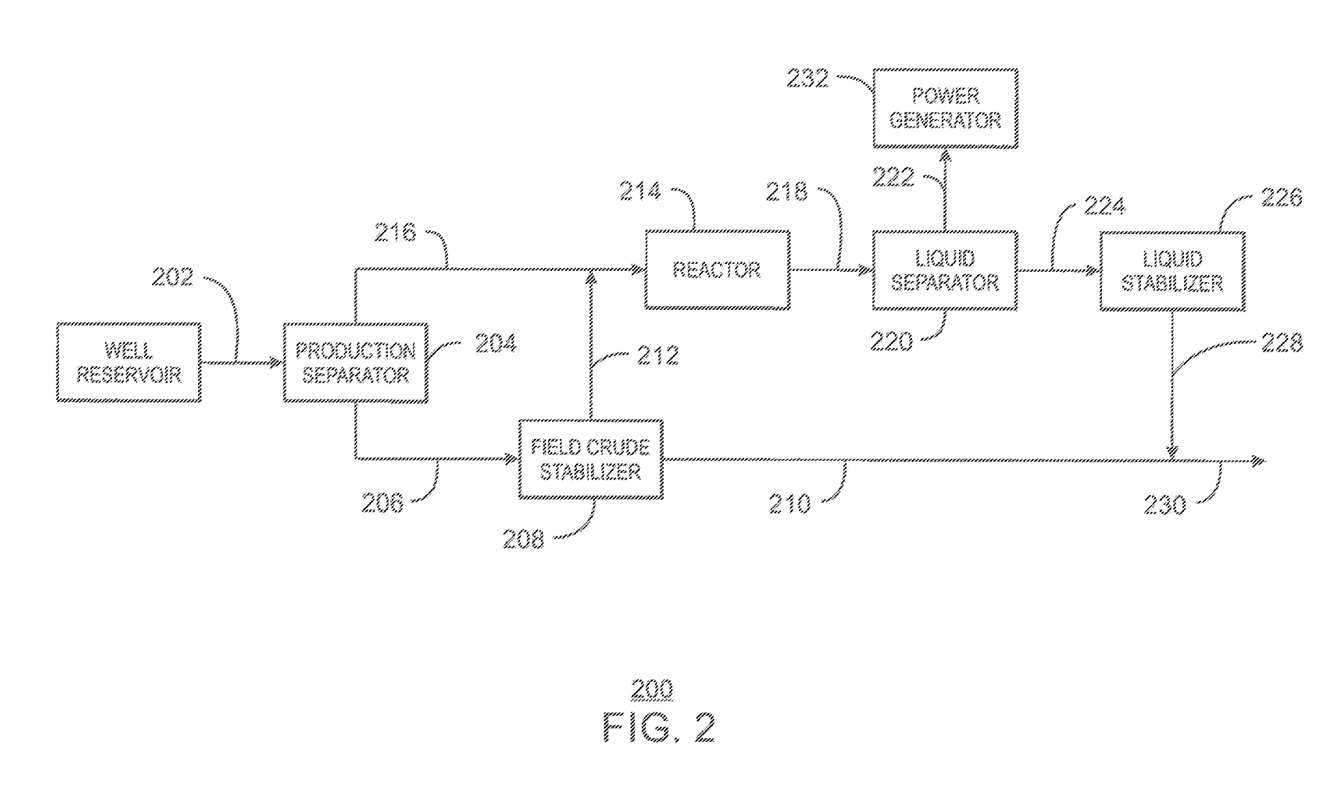
FIG. 2 is a block diagram of a system for producing a higher molecular weight hydrocarbons product.

FIG. 2 is a block diagram of a system 200 for producing a higher molecular weight hydrocarbons product. As shown in FIG. 2, a raw hydrocarbon 202 may be produced from a reservoir and may flow into a production separator 204. In some embodiments, the raw hydrocarbon 202 may contain crude oil and raw natural gas along with water, trace organic compounds, trace metals, and other entrained liquids and solids. A crude oil stream 206 can be taken from the bottom of the separator 204. The crude oil stream 206 can be directed to a field crude stabilizer 208, where water, light hydrocarbons, and gas contaminants are boiled off to produce a stabilized crude oil liquid stream 210. As shown in FIG. 2, an overhead gas stream 212 from the field crude stabilizer 208 may be directed to a reactor 214.

A raw natural gas stream 216 can be taken from the top of the separator 204 and combined with the overhead gas stream 212 before being flowed into the reactor 214. In various embodiments, the stream 216 may include methane, ethane, propane, butanes, nitrogen, carbon dioxide, and hydrogen, among other components. Within the reactor 214, conversion reactions may enable the conversion of lower molecular weight hydrocarbons in the raw natural gas to higher molecular weight hydrocarbons. In some embodiments, the lower molecular weight hydrocarbons may include methane and $C_2$ to $C_{5+}$ hydrocarbons and the higher molecular weight hydrocarbons may include $C_6$ to $C_9$ aromatics. In some examples, the overhead gas stream 212 may include sulfur compounds, such as mercaptans, sulfides, and other organosulfur compounds, in addition to hydrogen sulfide ($H_2S$). The organosulfur compounds may be at least partially converted in the reactor, forming further amounts of $H_2S$.

A stream 218 containing higher molecular weight hydrocarbons may flow from the reactor 214 and into a liquid separator 220. As shown in FIG. 2, the liquid separator 220 may separate the higher molecular weight hydrocarbons containing stream 218 into a tail gas stream 222 and a liquid hydrocarbons stream 224. The product value and transportability of a hydrocarbons stream in liquid form may be enhanced since liquid hydrocarbons can achieve a higher reduction in volume than hydrocarbons in gas form. Thus, it may be more cost effective to recover the natural gas and convert it into a liquid hydrocarbons stream, instead of flaring the natural gas, since it can now be transported by methods other than pipelines.

To reduce the volatility of the liquid hydrocarbons stream 224 during transportation, the liquid hydrocarbons stream 224 may be subjected to liquid stabilization. A liquid stabilizer 226 may operate at a low pressure to remove any volatile hydrocarbons and other gaseous contaminants within the liquid hydrocarbons stream 224 to produce a stabilized liquid hydrocarbons stream 228. As shown in FIG. 2, the stabilized liquid hydrocarbons stream 228 and the stabilized crude oil liquid stream 210 may merge together to form a liquid hydrocarbons product stream 230.

If the overhead gas stream 212 used as the feed contains organosulfur compounds, $H_2S$, or both, the resulting tail gas stream 222 may be treated to reduce or remove the $H_2S$, for example, if the concentration is greater than about 10 ppm, greater than 1000 ppm, or greater than 1%, depending on the sensitivity of the environment to $SO_x$'s formed from combusting the $H_2S$. The $H_2S$ can be removed by an adsorption column, a Claus process, a counter-current separation column, or any number of other techniques. If removal of the $H_2S$ is not convenient, for example, due to the remoteness of the site, treating the combustion exhaust to remove $SO_x$'s may be performed. This could be done by passing the exhaust gas through a water scrubbing column.

The tail gas stream 222 may be utilized for on-site generation of power to turn a power generator 232, where power may be generated and used by those in remote areas with limited access to power grids. This type of distributed power generation may be attractive since it can provide electricity that may be more reliable, more efficient, and cheaper than purchasing power from a centralized utility. Distributed power generation may also allow for increased local control over an electricity supply in remote areas, as well as, possibly lowering electricity losses during transmission. Additionally, the tail gas stream 222 may be used in heat integration to supply energy to the reactor 214. In some embodiments, the power generator may include a gas turbine or combustion engine.

The block diagram of FIG. 2 is not intended to indicate that the gas system 200 is to include all of the components shown in FIG. 2. Further, any number of additional components may be included within the method of producing a higher molecular weight hydrocarbons product. The system 200 may include any suitable types of heaters, chillers, condensers, pumps, compressors, other types of separation and/or fractionation equipment, among others, including any desirable purification steps prior to introducing the gas streams 216 and 212 into reactor 214. For example, the system 200 may include a suitable device or structure for condensing at least a portion of the gas streams 216 and/or 212, e.g., a pressure expansion device, an external refrigeration system, etc., prior to introduction into the reactor 214. Condensing in this way may create a liquid stream comprising higher molecular weight hydrocarbons and a gas stream comprising methane and other light components (e.g., nitrogen, helium, carbon dioxide, etc.). The liquid stream may be vaporized and introduced into the reactor 214 as feedstock, while the gas stream may be reinjected into the ground or used for another purpose. Those of skill in the art will recognize that this technique may be utilized to variably control the composition of the tail stream, and therefore the amount of co-produced power that may be generated.

Figure 3:
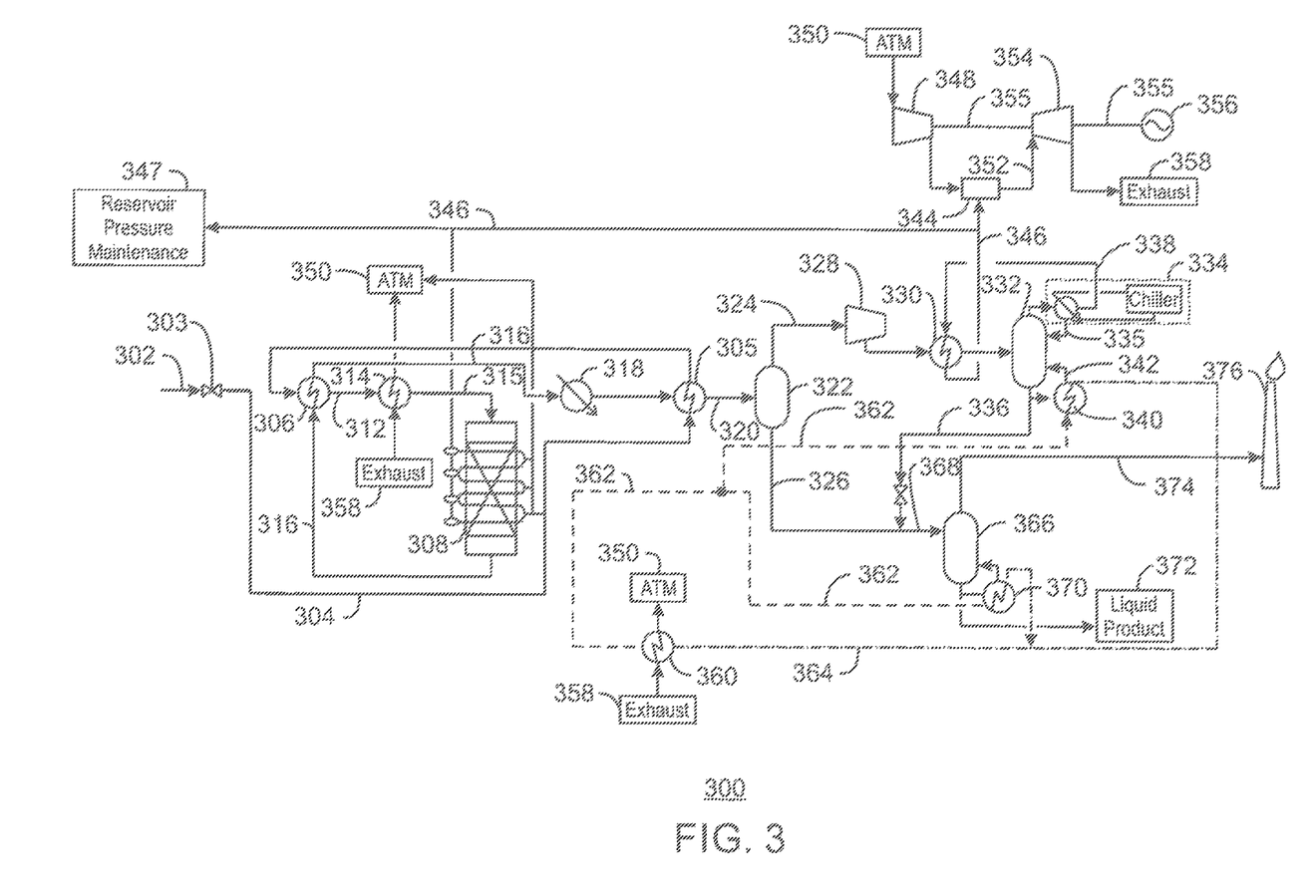
FIG. 3 is a simplified process flow diagram for a natural gas liquid recovery and stabilization unit including a distillation column.

FIG. 3 is a simplified process flow diagram 300 for a natural gas liquid recovery and stabilization unit including a distillation column. The raw natural gas stream 302 may include methane and lower molecular weight hydrocarbons, for example, $C_2$ to $C_{5+}$ hydrocarbons. The pressure of a raw natural gas stream 302 may be decreased by flashing the raw natural gas stream 302 across a valve 303, generating a low-pressure stream 304. The low-pressure stream 304 may be warmed in a product chiller 305 and heated in a reactor feed heater 306 to form a warm gas stream 312. The warm gas stream 312 can be further heated, for example, to operating temperatures of about 510° C. (about 950° F.) to about 600° C. (about 1100° F.) in a furnace heater 314 to form a reactor feed gas 315 that is fed to the reactor 308. The reactor feed gas 315 may undergo conversion reactions to form higher molecular weight hydrocarbons within the reactor 308. In some embodiments, the reactor feed gas 315 may be at a pressure range of about 280 KPa (about 40 psia) to about 480 KPa (about 70 psia). The pressure may be increased before entering the reactor 308, for example, by a compressor (not shown). A gaseous diluent, such as methane, may be blended with the raw natural gas stream 302 to reduce the formation of a byproduct, coke, which tends to accumulate on the catalyst pores and lower the reaction efficacy.

Any number of types of reactor 308 may be used, including a catalytic membrane reactor, a fixed-bed catalyst reactor, continuous catalytic regeneration reactor, or a fluidized bed reactor. The type of reactor utilized may depend on feed compositions and feed rates, conversion reaction temperatures, yield compositions, among other input and output factors. Moreover, the reaction rates and production yields may be enhanced by the use of a selective catalyst for the optimization of reaction conditions.

The catalyst can include at least one metal component on an inorganic support, such as amorphous silica, or alumina. The inorganic support may be a porous material such as a micro-porous crystalline material or a meso-porous material. Additionally, suitable molecular sieves may be utilized in the present catalyst and may include at least one medium pore molecular sieve having a Constraint Index of 2-12 (as defined in U.S. Pat. No. 4,016,218). Examples of such medium pore molecular sieves include ZSM-5, ZSM-11, ZSM-12, ZSM-22, ZSM-23, ZSM-35, ZSM-48, MCM-22 and MCM-49 and mixtures and intermediates thereof. ZSM-5 is described in detail in U.S. Pat. No. 3,702,886 and Re. 29,948. ZSM-11 is described in detail in U.S. Pat. No. 3,709,979. A ZSM-5/ZSM-11 intermediate structure is described in U.S. Pat. No. 4,229,424. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

The metal component of the catalyst may be present in an amount of at least 0.1 wt. %, such as from 0.1 to 5 wt. %, of the overall catalyst. The metal component may include one or more neutral metals selected from Groups 3 to 13 of the Periodic Table of the Elements, such as Ga, In, Zn, Cu, Re, Mo, W, La, Fe, Ag, Pt, Pd, and/or one or more oxides, sulfides and/or carbides of these metals. The metal component can be provided on the catalyst in any known manner, for example by impregnation or ion exchange of the molecular sieve with a solution of a compound of the relevant metal, followed by conversion of the metal compound to the desired form, namely neutral metal, oxide, sulfide and/or carbide. Part or all of the metal may also be present in a crystalline framework of the molecular sieve.

In a preferred embodiment, a bifunctional catalyst may be selected from the group consisting of Ga and/or In-modified ZSM-5 type zeolites, such as Ga and/or In-impregnated H-ZSM-5, Ga and/or In-exchanged H-ZSM-5, H-gallosilicate of ZSM-5 type structure and H-galloaluminosilicate of ZSM-5 type structure. These zeolites can also be prepared by methods known in the prior art.

For example, the bifunctional catalyst may contain tetrahedral aluminum or gallium, which is present in the zeolite framework or lattice. The bifunctional catalyst may also contain octahedral gallium or indium, which is not present in the zeolite framework, but present in the zeolite channels in close vicinity to the zeolitic protonic acid sites that may be attributed to the presence of tetrahedral aluminum and gallium in the catalyst. The tetrahedral or framework of Al or Ga can be responsible for the acid function of the catalyst and octahedral or non-framework Ga or In may be responsible for the dehydrogenation function of the catalyst. In a preferred embodiment, the bifunctional catalyst may include H-galloaluminosilicate of ZSM-5 type structure having framework (tetrahedral) Si/Al and Si/Ga mole ratios of about 10:1 to 100:1 and 15:1 to 150:1, respectively, and non-framework (octahedral) Ga of about 0.5 to 0 wt. %.

In addition to the molecular sieve and hydrogenation component, the catalyst may be composited with other materials, which may be resistant to the temperatures and other conditions employed in the conversion reaction. Such other materials can include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst.

Additionally, inactive materials may serve as diluents to control the amount of conversion so that products can be obtained without employing other means for controlling the rate of reaction. These materials may be incorporated into naturally-occurring clays, e.g., bentonite and kaolin, to improve the crush strength of the catalyst under commercial operating conditions and function as binders or matrices for the catalyst. The relative proportions of molecular sieve and inorganic oxide matrix may vary, with the sieve content ranging from about 1 to about 90 percent by weight and more usually, particularly, when the composite is prepared in the form of beads, in the range of about 2 to about 80 weight percent of the composite.

The product of the conversion reactions in the reactor 308 may include a higher molecular weight hydrocarbons stream 316, e.g., including $C_6$ to $C_9$ aromatics, and other entrained solid and liquid hydrocarbons. The higher molecular weight hydrocarbons stream 316 may be cooled upon exiting the reactor 308 by an air cooler 318. For initial liquids recovery, the higher molecular weight hydrocarbons stream 316 may further be chilled to a temperature range of about 10° C. (50° F.) to about 26° C. (80° F.) by exchanging heat with the low-pressure stream 304 in the product chiller 305. The chilled higher molecular weight hydrocarbons stream 320 may then flow into a gas liquid separator 322 for the initial recovery of liquid hydrocarbons. During separation, a tail gas stream 324 may be produced overhead and a liquid hydrocarbons stream 326 may be produced as a bottoms stream.

The tail gas stream 324 can be compressed in a tail gas compressor 328 and chilled in a heat exchanger 330 to remove the heat of compression. From the heat exchanger 330, the tail gas 324 may be sent to a distillation column 332. An overhead gas stream from the distillation column 332 may be chilled in a refrigeration cycle 334, and returned to the distillation column 332 as a reflux stream 335. A liquid stream 336 can be taken from the bottom of the distillation column 332 at a relatively high pressure (e.g. 300 psia). A portion of the liquid stream 336 may be passed through a reboiler 340 and returned as a vapor 342 to the column 332. The remainder of the liquid stream 336 can be combined with the liquid hydrocarbons stream 326 from the two-phase separator 322.

A product gas stream 338 taken from the overhead of the distillation column 332 can be heated against the hot tail gas stream from the compressor 328 forming a fuel gas stream 346. The fuel gas stream 346 may include methane, ethane, as well as non-hydrocarbon gases such as hydrogen, carbon dioxide, hydrogen sulfide, and nitrogen. The fuel gas stream 346 can be burned in a combustor 344 to power a gas turbine generator 356.

A portion of the fuel gas stream 346 can be sent to a pressure maintenance system 347 to be re-injected into the reservoir 102 (FIG. 1) to maintain the pressure of a gas cap located within the reservoir 102 or recycled to the front to mix with the inlet feed gas. Likewise, as stated earlier the fuel gas may be divided into hydrogen rich and hydrogen poor streams, so that only the hydrogen poor stream is reinjected, if required. Further, the fuel gas stream 346 may be used to supply heat to the reactor 308, for example, by being combusted in a burner to heat the stream 346 in the furnace heater 314.

In the gas turbine generator 356, an air compressor 348 can compress an air stream taken from the atmosphere 350, and feed the compressed stream to the combustor 344. The hot gas stream 352 from the combustion is flowed through a turbine expander 354 to turn a shaft 355. The shaft 355 can provide the power to turn the air compressor 348, closing the Brayton cycle. Further, the shaft 355 can be used to drive the generator 356, providing electricity that can be used on-site, placed on a power grid, or both. The gas turbine generator 356 may burn up to 1% hydrogen sulfide in the hot gas stream 352. If desired, a gas treatment system can be added to remove at least a portion of the hydrogen sulfide, or other impurities, to generate acceptable gas turbine performance or lower exhaust pollutants.

After flowing through the turbine expander 354, the pressure of a hot gas stream 352 is lowered, forming an exhaust 358. The heat in the exhaust 358 may be used in other processes in the facility. For example, a portion of the exhaust 358 can be used to heat the reactor feed gas 315 in the furnace heater 314, before being released to the atmosphere 350. This may be implemented, for example, by flowing the warm gas stream 312 through a tube bundle in a heat recovery unit placed at the end of the expander turbine 354. As described herein, the furnace heater 314 is not limited to using the exhaust 358, but may be heated by a burner that combusts a portion of the fuel gas stream 346. Further, the reactor 308 may also contain a tube bundle to maintain a reasonable isothermal reactor. A fluid from the reactor 308 may be pulled and re-injected into the furnace heater 314 and into multiple points of heat inputs within the reactor 308. The tube bundle of the reactor 308 may be located on the outside of the reactor 308 and heated by an external burner.

Another portion of the exhaust 358 may be used to heat a heat exchange fluid in a heat exchanger 360, before being released to the atmosphere 350. A hot fluid 362 can be used to heat any number of other systems, as described herein. The resulting cool fluid 364 can then be returned to the heat exchanger 360 to close the cycle. In addition, a convective section the furnace heater 314 could be used to supply the heat source from stream 362.

The gas turbine generator may operate on the same concept as larger centralized gas turbine generators as used in many processing facilities. However, instead of being located in a centralized plant, the gas turbine generator may be located in close proximity to where the electricity being generated can be used. Thus, the tail gas may provide power to remote locations without a substantial power generation system making small electrical grids possible, or increasing the capacity of existing electrical grids.

The liquid hydrocarbons stream 326 from the two-phase separator 322, combined with the liquid stream 336 from the distillation column 322, forming a combined stream 368, can be flowed into a stabilizer vessel 366, for example, operating in a pressure range of about 207 KPa (about 30 psia) to about 414 KPa (about 60 psia). The combined stream 368 may include a liquid hydrocarbons mixture of higher molecular weight hydrocarbons with lesser amounts of light hydrocarbons and other gases. A reboiler 370 can be used to heat the liquid in the stabilizer vessel 366, for example, with heat from the hot fluid 362. The heat applied to the stabilizer vessel 366 strips the light hydrocarbons from the combined stream 366, forming a liquid product 372 that meets vapor pressure specifications for transportation. A small quantity of overhead vapor 374 from the stabilizer vessel 366 may be sent to a flare 376, for example, if recovery and recompression is not economical. The liquid product 372 may be sold as a separate product, or may be mixed into a crude oil stream The process flow diagram of FIG. 3 is not intended to indicate that the system 300 is to include all of the components shown in FIG. 3. Further, any number of additional components may be included in the system 300. For example, the system 300 may include any suitable types of heaters, chillers, condensers, pumps, compressors, other types of separation and/or fractionation equipment, valves, pumps, pressure-measuring devices, or temperature-measuring device, among others.

Figure 4:
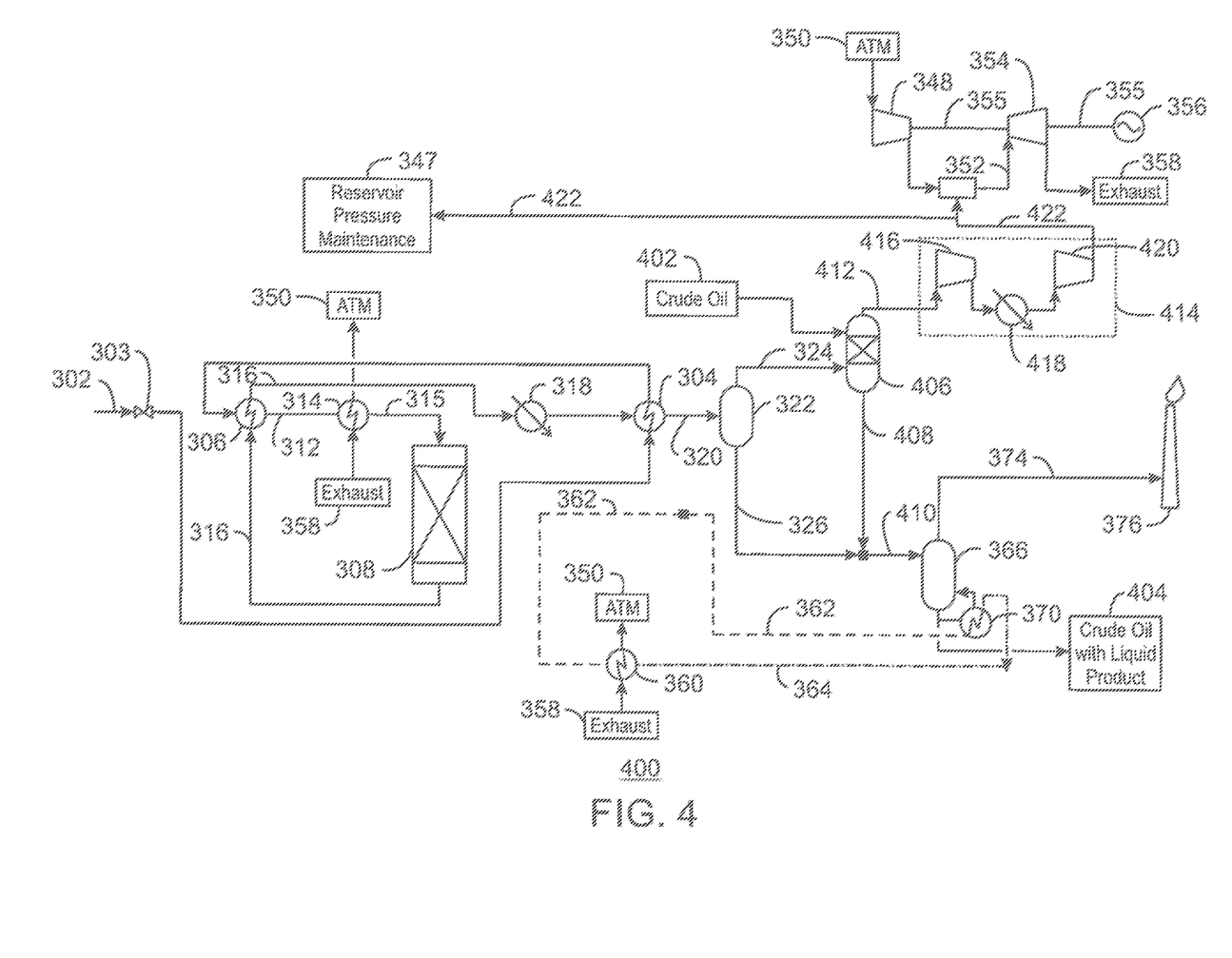
FIG. 4 is a process flow diagram for a natural gas liquid recovery and stabilization unit including a crude wash.

FIG. 4 is a process flow diagram 400 for a natural gas liquid recovery and stabilization unit including a crude or condensate wash. Like numbered items are as described with respect to FIG. 3. Although similar to FIG. 3, the system in FIG. 4 washes the tail gas stream 324 with crude oil 402 to remove the liquid hydrocarbons, resulting in crude oil or condensate product 404 that includes the liquid hydrocarbons.

To perform the wash, the tail gas stream 324 if fed into the bottom of a crude wash column 406. The crude oil 402 is fed into the top of the crude wash column 406, solubilizing the higher molecular weight hydrocarbons in a counter current extraction. The crude oil 402 and solubilized hydrocarbons are recovered as a bottom liquids stream 408. The crude oil 402 for the crude wash may include a produced crude oil, or any other available hydrocarbon stream such as a stabilized condensate.

As shown in FIG. 4, the liquid hydrocarbons stream 326 from the two-phase separator 322 and a liquid bottoms stream 408 from the crude wash column 406 may flow into a stabilizer vessel 366 as a combined stream 410. As described with respect to FIG. 3, the light hydrocarbons and trace gases can be stripped from the combined stream 410 to produce a crude oil product 404 that contains the higher molecular weight hydrocarbons formed in the process.

A vapor stream 412 can be taken from the top of the crude wash column 406 and flowed into a multi-stage compressor unit 414. The multi-stage compressor unit 414 can be used to compensate for low pressures that may be used during the crude oil wash. In the multi-stage compressor unit 414, a first compressor 416 may increase the pressure of the vapor stream 412 from a pressure between about 280 KPa (about 40 psia) and about 480 KPa (about 70 psia) up to a pressure between about 670 KPa (about 100 psia) and about 3500 KPa (about 500 psia). An inter-cooler 418 may be used to remove the heat of compression from the vapor stream, before it is fed to a second compressor 420. The second compressor 420 may further increase the pressure to about 3500 KPa (about 500 psia) or higher, to produce a high pressure fuel gas 422 that can be combusted in the combustor 344, as described with respect to FIG. 3. As for the system 300 in FIG. 3, a portion of the high-pressure fuel gas 422 can be sent to a pressure maintenance system 347 or recycled to the feed stream. Further, a portion may be combusted in a burner to heat the furnace heater 314, instead of, or in addition to, the exhaust 358 from the gas turbine generator.

The process flow diagram of FIG. 4 is not intended to indicate that the system 400 is to include all of the components shown in FIG. 4. Further, any number of additional components may be included within the system 400. For example, the system 400 may include any suitable types of heaters, chillers, condensers, pumps, compressors, other types of separation and/or fractionation equipment, valves, pumps, pressure-measuring devices, or temperature-measuring device, among others.

Figure 5:
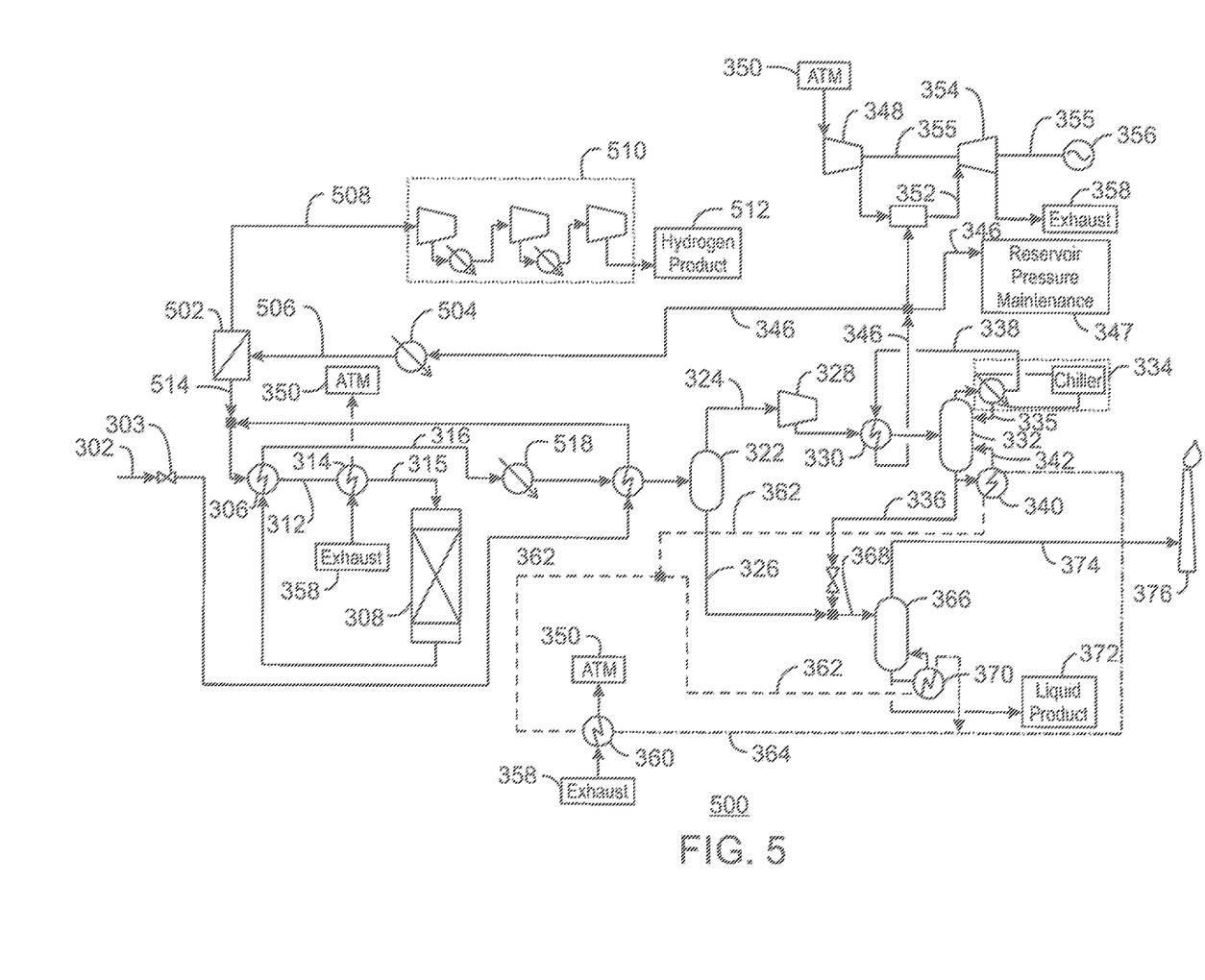
FIG. 5 is a process flow diagram for a natural gas liquid recovery and stabilization unit that recovers hydrogen from the tail gas.

FIG. 5 is a process flow diagram 500 for a natural gas liquid recovery and stabilization unit that recovers hydrogen from the tail gas. Like numbered items are as described with respect to FIG. 3. Although similar to FIG. 3, FIG. 5 incorporates a hydrogen recovery system to separate hydrogen from the tail gas stream.

As discussed with respect to FIG. 3, a fuel gas stream 346 may be formed in a process that creates higher molecular weight hydrocarbons. The fuel gas stream 346 primarily includes methane, but may also include other gases, such as hydrogen formed in the reaction. The hydrogen may provide a useful feedstock, for example, to place a chemical plant near the site of the well. Accordingly, recovery of the hydrogen can increase the value of the products produced.

To recover the hydrogen, a portion of fuel gas stream 346 may be redirected to a hydrogen separation unit 502, for example, based on membrane technology although any number of technologies may be used. A membrane separation provides a simpler technology, which is more suited to use in remote locations. A membrane separation is generally based on the difference between in permeation rates between the hydrogen and impurities across a gas-permeable membrane. Hydrogen, which has a higher permeability, may diffuse through the membrane from the high-pressure side to the low-pressure side. Before entering the hydrogen separation unit 502, the fuel gas stream 346 may be cooled using an air cooler 504 to produce a cool gas stream 506. A low-pressure, hydrogen-enriched stream 508 that may be formed from the low-pressure side of the membrane may be compressed in a multi-stage compressor unit 510 to produce compressed hydrogen 512. The compressed hydrogen 512 can be used at the site for chemical reactions, sold to market, or recombined with the fuel gas stream 346, for example, to enhance the BTU content of the fuel gas. A hydrogen-depleted stream 514 may be mixed with the raw natural gas stream 302 for additional conversion within a reactor 308 or reinjected into the reservoir, as required.

The process flow diagram of FIG. 5 is not intended to indicate that the system 500 is to include all of the components shown in FIG. 5. Further, any number of additional components may be included within the system 500. For example, the system 500 may include any suitable types of heaters, chillers, condensers, pumps, compressors, other types of separation and/or fractionation equipment, valves, pumps, pressure-measuring devices, or temperature-measuring device, among others.

Figure 6:
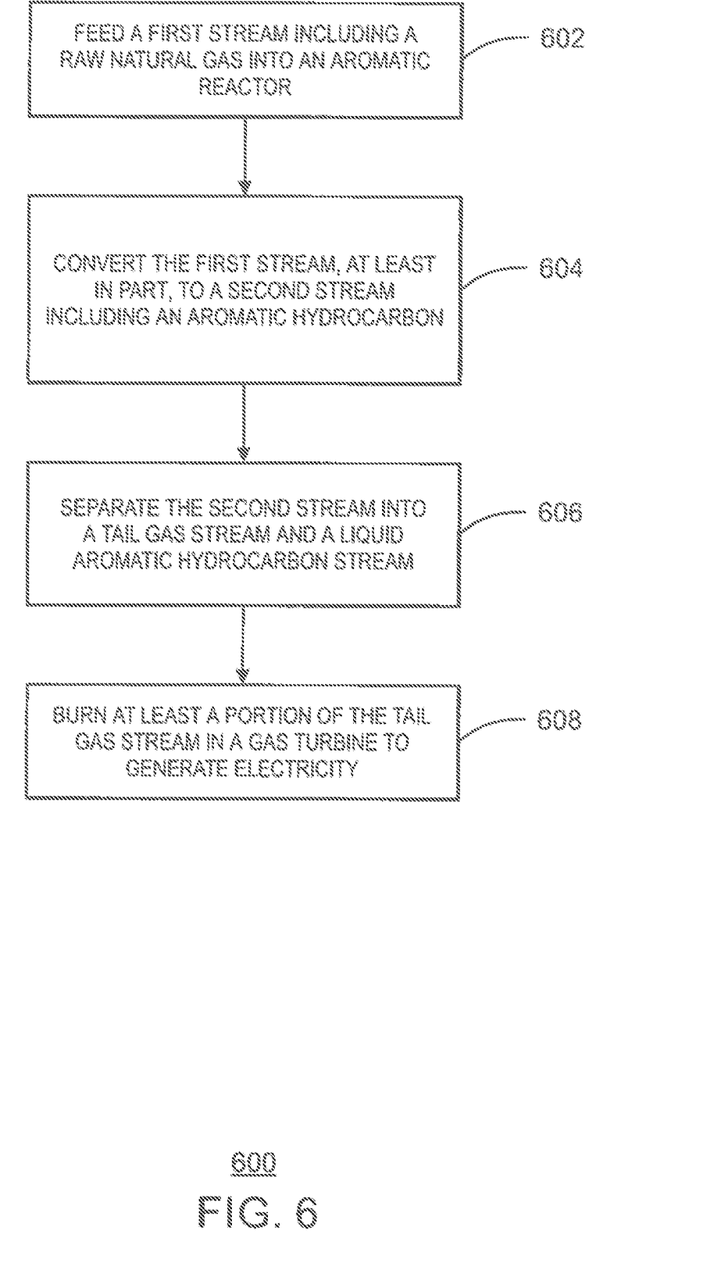
FIG. 6 is a flow block diagram of a method for producing liquid hydrocarbons.

FIG. 6 is a flow block diagram of a method 600 for producing an aromatic hydrocarbon. According to embodiments described herein, the method may produce an aromatic hydrocarbon and generate electricity from a tail gas stream.

The method 600 begins at block 602, when a first stream including raw natural gas is fed into an aromatic reactor. At block 604, the first stream is converted, at least in part, to a second stream including the aromatic hydrocarbon. At block 606, the second stream is separated into a tail gas stream and a liquid aromatic hydrocarbon stream. At block 608, at least a portion of the tail gas stream is burned in a gas turbine to generate electricity.

Simulations

Simulations were conducted to test the operation of the system described herein. The following Table 1 provides simulated data at various stages of the system for producing a higher molecular weight hydrocarbons product. In particular, the case studies included the flow rate, the volumetric flow, the molecular weight, and the composition of the reactor feed for the reactor feed, the liquid hydrocarbons product, the fuel gas, and the flare gas. Further, for various stages of the system, a particular catalyst was provided based on conversion rates measured against the varying flow rates, the volumetric flows, the molecular weights, and the compositions of the reactor feed As shown in Table 1, Case 1 and Case 2 represent the use of Catalyst 1 during simulation. Case 1 depicts separation of a tail gas stream from a liquid hydrocarbons stream using a liquid separator or a demethanizer. Conversely, Case 2 depicts separation of a tail gas stream from a liquids hydrocarbons stream using a crude wash column. Particularly, FIG. 3 of the present disclosure illustrates Case 1 and FIG. 4 of the present disclosure illustrates Case 2.

Case 3 represents a simulation with little to no conversion using Catalyst 2. Moreover, Cases 4 and 5 depict conversion using Catalyst 3. Additionally, FIG. 5 also illustrates Case 5 where recovered hydrogen is remixed with a fuel gas stream, where the combined streams are feed to a gas turbine for power production.

While the present techniques may be susceptible to various modifications and alternative forms, the embodiments discussed above have been shown only by way of example. However, it should again be understood that the techniques is not intended to be limited to the particular embodiments disclosed herein. Indeed, the present techniques include all alternatives, modifications, and equivalents falling within the true spirit and scope of the appended claims.

TABLE 1

Simulations of Hydrocarbon Conversion

| | Case | | | | |
|---|---|---|---|---|---|
| | 1<br>Catalyst 1 | 2<br>Catalyst 1 | 3<br>Catalyst 2 | 4<br>Catalyst 3 | 5<br>Catalyst 3 |
| Reactor Feed | Demethanizer | Crude Wash | | | Recycle |
| Mass Rate (kg/hr) | 74,886 | 74,886 | 74,886 | 55,333 | 131,988 |
| Std. Vol. Flow (m3/hr) | 58,994 | 58,994 | 58,994 | 58,994 | 146,304 |
| Mol Weight (g/gmol) | 30.07 | 30.07 | 30.07 | 22.22 | 21.27 |
| Composition (mol %) | | | | | |
| N2 | 2.70 | 2.70 | 2.70 | 1.70 | 1.91 |
| CO2 | 0.75 | 0.75 | 0.75 | 0.60 | 0.69 |
| H2 | 0.00 | 0.00 | 0.00 | 0.00 | 1.92 |
| C1 | 44.80 | 44.80 | 44.80 | 73.60 | 73.84 |
| C2 | 23.10 | 23.10 | 23.10 | 13.80 | 12.86 |
| C3 | 18.00 | 18.00 | 18.00 | 6.00 | 5.25 |
| C4 | 7.30 | 7.30 | 7.30 | 2.60 | 2.14 |
| C5-C7 | 3.35 | 3.35 | 3.35 | 1.70 | 1.38 |
| Liquid Product | | | | | |
| Mass Rate (kg/hr) | 35,101 | 33,461 | 35,975 | 22,378 | 50,846 |
| Volume (m3/hr) | 40.9 | 38.8 | 41.9 | 25.9 | 58.7 |
| Mol Weight (g/gmol) | 94.60 | 159.7 | 94.50 | 91.96 | 91.76 |
| API | 52.0 | 79.78 | 52.0 | 52.1 | 52.1 |
| TVP (bara) | 0.72 | 0.72 | 0.72 | 0.72 | 0.73 |
| Composition (mol %) | | Blended w/Crude | | | |
| C2 | 0.52 | 0.89 | 0.54 | 0.66 | 0.65 |
| C3 | 2.14 | 0.02 | 2.11 | 0.74 | 0.70 |
| C4 | 1.07 | 0.78 | 1.05 | 0.40 | 0.36 |
| C5-C7 | 1.52 | 0.97 | 1.48 | 1.01 | 0.89 |
| Benzene | 23.91 | 13.27 | 23.3 | 31.96 | 32.55 |
| Toluene | 23.19 | 12.74 | 25.06 | 31.35 | 31.90 |
| Ethylbenzene | 14.2 | 7.81 | 13.85 | 10.51 | 10.10 |
| O-xylene | 14.2 | 7.81 | 13.85 | 10.22 | 9.98 |
| P-xylene | 12.19 | 5.72 | 11.88 | 8.99 | 8.88 |
| 1,3,5-Trimethylbenzene | 7.05 | 3.87 | 6.87 | 4.09 | 3.92 |
| Fuel Gas | | | | | |
| Mass Rate (kg/hr) | 39,628 | 41,294 | 38,759 | 32,905 | 59,686 |
| Std. Vol. Flow (m3/hr) | 83,771 | 82,591 | 83,771 | 75,512 | 155,743 |
| Mol Weight (g/gmol) | 11.24 | 11.76 | 10.90 | 10.28 | 9.06 |
| Composition (mol %) | | | | | |
| N2 | 1.91 | 1.91 | 1.89 | 1.32 | 1.28 |
| CO2 | 0.52 | 0.52 | 0.52 | 0.46 | 0.45 |
| H2 | 52.84 | 50.97 | 55.06 | 51.70 | 58.33 |
| C1 | 33.43 | 34.99 | 31.32 | 39.98 | 34.87 |
| C2 | 7.37 | 7.33 | 7.31 | 4.95 | 3.91 |
| C3 | 3.40 | 3.31 | 3.37 | 1.27 | 0.95 |
| C4 | 0.40 | 0.37 | 0.40 | 0.17 | 0.12 |
| C5-C7 | 0.08 | 0.50 | 0.08 | 0.06 | 0.04 |
| Benzene | 0.05 | 0.02 | 0.05 | 0.08 | 0.05 |
| Toluene | 0.0001 | 0 | 0.0002 | 0.0004 | 0.0002 |
| Flare | | | | | |
| Mass Rate (kg/hr) | 157 | 131 | 152 | 49 | 133 |
| Mol Weight (g/gmol) | 25.70 | 18.89 | 25.63 | 18.92 | 19.46 |
| Composition (mol %) | | | | | |
| N2 | 0.58 | 1.31 | 0.61 | 0.70 | 0.74 |
| CO2 | 2.89 | 1.14 | 2.96 | 1.16 | 1.45 |
| H2 | 5.44 | | 6.05 | 10.24 | 9.77 |
| C1 | 38.77 | 67.26 | 38.00 | 71.16 | 70.1 |
| C2 | 41.18 | 12.42 | 41.34 | 11.49 | 12.14 |
| C3 | 8.86 | 4.67 | 8.75 | 2.88 | 3.00 |
| C4 | 0.96 | 0.57 | 0.95 | 0.42 | 0.42 |
| C5-C7 | 0.23 | 0.12 | 0.23 | 0.16 | 0.16 |
| Benzene | 0.79 | 0.67 | 0.79 | 1.35 | 1.63 |
| Toluene | 0.20 | 0.16 | 0.22 | 0.36 | 0.45 |

What is claimed is:

1. An integrated method for producing an aromatic hydrocarbon and generating electricity from a tail gas stream, the method comprising:
   feeding a first stream comprising raw natural gas into an aromatic reactor;
   converting the first stream, at least in part, to a second stream comprising the aromatic hydrocarbon;
   separating the second stream into the tail gas stream and a liquid aromatic hydrocarbon stream;
   flowing the tail gas stream to a crude wash column, wherein liquids in the tail gas stream are solubilized with a crude oil wash and recovered as a liquid product, wherein the liquid product is combined with the liquid aromatic hydrocarbon stream; and
   burning at least a portion of the tail gas stream in a gas turbine to generate the electricity.

2. The method of claim 1, wherein the first stream includes methane, $C_2$-$C_{5+}$ hydrocarbons, CO, $CO_2$, $N_2$, $H_2S$, organic sulfur compounds, or any combinations thereof.

3. The method of claim 1, comprising flowing the first stream through a molecular sieve in the aromatic reactor.

4. The method of claim 1, wherein the second stream includes $C_6$ to $C_9$ aromatics.

5. The method of claim 1, wherein components in the first stream are converted at a temperature range from 750° F. to 1200° F.

6. The method of claim 1, comprising heating, in a furnace, the first stream with an exhaust heat from the burning of the portion of the tail gas stream in the gas turbine.

7. The method of claim 1, comprising heating, in a heat exchanger, a a cooled heat exchange fluid with an exhaust from the burning of the portion of the tail gas stream in the gas turbine.

8. The method of claim 1, comprising compressing and sending the tail gas stream to a distillation column, wherein a compressed tail gas stream includes one or more of methane ($CH_4$), ethane ($C_2H_6$), carbon dioxide, carbon monoxide, hydrogen sulfide, nitrogen, or hydrogen.

9. The method of claim 1, comprising recycling at least a portion of the tail gas stream into the aromatic reactor as a diluent.

10. The method of claim 1, comprising stabilizing the liquid aromatic hydrocarbon stream in a stabilizer.

11. The method of claim 1, comprising transporting the liquid aromatic hydrocarbon stream to market.

* * * * *